United States Patent
Shapiro

(10) Patent No.: US 6,555,718 B1
(45) Date of Patent: Apr. 29, 2003

(54) PROCESS FOR PREPARING 3,3',6,6'-TETRAALKYL-2,2'-BIPHENOLS AND 3,3',6,6'-TETRAALKYL-5,5'-DIHALO-2,2'-BIPHENOLS

(75) Inventor: Rafael Shapiro, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/235,413

(22) Filed: Sep. 5, 2002

Related U.S. Application Data

(62) Division of application No. 09/994,098, filed on Nov. 26, 2001, now Pat. No. 6,489,517.

(51) Int. Cl.[7] .............................................. C07C 39/12
(52) U.S. Cl. ...................................................... 568/730
(58) Field of Search .......................................... 568/730

(56) References Cited

U.S. PATENT DOCUMENTS

| | | | |
|---|---|---|---|
| 2,041,593 A | * | 5/1936 | Burroughs |
| 3,542,882 A | * | 11/1970 | Ashall |
| 3,839,469 A | * | 10/1974 | Laufer |
| 3,920,757 A | * | 11/1975 | Watson |
| 3,931,340 A | * | 1/1976 | Nishihara |
| 4,245,127 A | * | 1/1981 | Matsumoto |
| 5,696,280 A | * | 12/1997 | Shapiro |
| 5,847,222 A | * | 12/1998 | Yokozawa |
| 6,171,996 B1 | * | 1/2001 | Garner |

OTHER PUBLICATIONS

D.R. Stevens, Ind. Eng. Chem. 1943, Separation of Individual CRESOLS and XYLENOLS from their Mixtures, vol. 35, No. 6, pp. 655–658.

Parc. Rev. Inst. Fr. Pet. 1960, pp. 680 (Translated Attached).

Blackstock et al., Aust. J. Chem. 1973, Side Chain Nitration of Polymethylbenzenes in NitricAcid–Acetic Anhydride Mixtures, vol. 26, pp. 775–783.

Armstrong et al., J. Chem. Soc., Perkin Trans. II, 1983, Oxidative Coupling of Phenols. Part 10.[1] The Role of Steric Effects in the Formation of C–O Coupled Products, pp. 587–589.

Keiko Kushioka, J. Org. Chem. 1983, Catalytic Activity of Copper(II)–Ethylenediamine Complexes in Autoxidation of Phenols, vol. 48, 4948–4950.

Keiko Kushioka, J. Org. Chem. 1984, Autoxidation of Phenols Catalyzed by Copper (II)–Ethylenediamine Complexes: The Reaction Mechanism, vol. 49, pp. 4456–4459.

W. D. Watson, J. Org. Chem. 1985, Regioselective Para Chlorination of Activated Aromatic Compounds, vol. 50, pp. 2145–2148.

Noji et al., Tetrahedron Letters, 1994, A New Catalytic System for Aerobic Oxidative Coupling of 2–Naphthol Derivatives by the Use of CuCl–Amine Complex: A Practical Synthesis of Binaphthol Derivatives, vol. 35, No. 43, pp. 7983–7984.

* cited by examiner

*Primary Examiner*—Michael L. Shippen
(74) *Attorney, Agent, or Firm*—Gerald E. Deitch

(57) ABSTRACT

A process for making a compound of the formula I

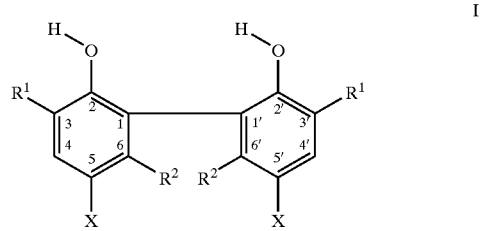

7 Claims, No Drawings

PROCESS FOR PREPARING 3,3',6,6'-TETRAALKYL-2,2'-BIPHENOLS AND 3,3',6,6'-TETRAALKYL-5,5'-DIHALO-2,2'-BIPHENOLS

CROSS REFERENCE TO RELATED APPLICATIONS

This is a Divsional case, filed under 37 C.F.R. 1.153(b) and claiming priority to U.S. patent application Ser. No. 09/994,098 filed Nov. 26, 200 now U.S. Pat. No. 6,489,517.

FIELD OF THE INVENTION

This invention relates to a process for preparing 3,3',6,6'-tetraalkyl-2,2'-biphenols and 3,3',6,6'-tetraalkyl-5,5'-dihalo-2,2'-biphenols.

BACKGROUND OF THE INVENTION

Substituted biphenols such as 3,3',6,6'-tetraalkyl-2,2'-biphenol; 3,3',4,4',5,5',6,6'-octaalkyl-2,2'-biphenols; 3,3',5,5',6,6'-hexaalkyl-2,2'-biphenols; 3,3',5,5'-tetraalkyl-2,2'-biphenol; 3-alkyl-5,5',6,6',7,7'8,8'-octahydro-2,2'-binaphthol; 3,3'-dialkyl-5,5',6,6',7,7'8,8'-octahydro-2,2'-binaphthol and 3,3'6,6'-tetralkyl-5,5'-dihalo-2,2'-biphenol are compounds that can be used to make phosphorus-based catalyst ligands. Such ligands include phosphines, phosphinites, phosphonites, and phosphites. Mono (phosphorous) ligands are compounds that contain a single phosphorus atom which serves as a donor to a transition metal, while bis(phosphorus) ligands, in general, contain two phosphorus donor atoms and typically form cyclic chelate structures with transition metals.

In general, biphenols can be made by the oxidative coupling of (mono)phenols, but often other types of products, such as ketones, are obtained, and/or overall yields are poor for other reasons.

Phenols can be oxidatively coupled to make the corresponding biphenols by the use of a variety of oxidizing agents, such as nitric acid, ferric chloride, potassium ferricyanide, chromic acid, 2,3-dichloro-5,6-dicyanobenzoquinone and di-t-butyl peroxide. 2,2'-Dihydroxy-3,3'-di-isopropyl-6,6'-dimethylbiphenyl can be prepared from 2-isopropyl-5-methyl-phenol with 2,3-dichloro-5,6-dicyanobenzoquinone or di-t-butyl peroxide. See Tetrahedron, 1875, 1971 and J. Chem. Soc., Perkin Trans. II, 587, 1983. Some of the oxidants and/or co-catalysts involve the use of relatively expensive and/or explosive (peroxides) compounds, which pose disadvantages for large scale commercial use.

Phenols can also be oxidatively coupled using a combination of a transition metal catalyst and an oxidizing agent such as persulfate anion or oxygen. See U.S. Pat. Nos. 6,077,979; 4,139,544; 4,132,722; 4,354,048; and 4,108,908. See also J. Org. Chem. 1984, 49, 4456 and J. Org. Chem. 1983, 48, 4948. The cited patents disclose the use of oxygen as an oxidizing agent with various copper complexes as catalysts (copper chromite; copper acetate with sodium mercaptoacetate; copper acetate with pentasodium/diethylenetriaminepentacetate; copper acetate with 1,3-diamino-2-hydroxypropane-tetracetic acid). The examples in the patents disclose the use of 2,6-disubstituted phenol or 2,4-di-tert-butylphenol.

The use of copper amine catalysts, with oxygen as an oxidizing agent, has been described in connection with the oxidative coupling of 2,4-di-tert-butylphenol, 2-methyl-4-tert-butylphenol, 2-chlor-4-tert-butylphenol and 4-tert-butylphenol. See J. Org. Chem. 1984, 49, 4456 and J. Org. Chem. 1983, 48, 4948.

There is a continuing need in the art for methods for making with decent yields substituted biphenols suitable for making phosphorous-based catalyst ligands.

SUMMARY OF THE INVENTION

In its first aspect, the present invention is a process for making a compound of the formula I wherein $R^1$ is $C_1$ to $C_{10}$ primary or secondary alkyl or cycloalkyl, $R^2$ is $C_1$ to $C_{10}$ primary or secondary alkyl or cycloalkyl, and X is H, Cl, Br, or I, comprising:
(1) when X is Cl
  (a) chlorinating a compound of the formula II at the 4-position thereof to produce a compound of the formula III wherein X is Cl,
  (b) oxidatively coupling the compound of the formula III wherein X is Cl to produce a compound of the formula I wherein X is Cl;
(2) when X is H
  (a) chlorinating a compound of the formula II at the 4-position thereof to produce a compound of the formula III wherein X is Cl,
  (b) oxidatively coupling the compound of the formula III wherein X is Cl to produce a compound of the formula I wherein X is Cl, and
  (c) dechlorinating the compound of the formula I wherein X is Cl to produce a compound of the formula I wherein X is H; or (3) when X is Br or I
- (a) chlorinating a compound of the formula II at the 4-position thereof to produce a compound of the formula III wherein X is Cl,
- (b) oxidatively coupling the compound of the formula III wherein X is Cl to produce a compound of the formula I wherein X is Cl,
- (c) dechlorinating the compound of the formula I wherein X is Cl to produce a compound of the formula I wherein X is H, and
- (d) substituting Br or I, respectively, for H at the 5 and 5' positions of the compound of the formula I wherein X is H.

In its second aspect, the present invention is a process for making a compound of the formula IV

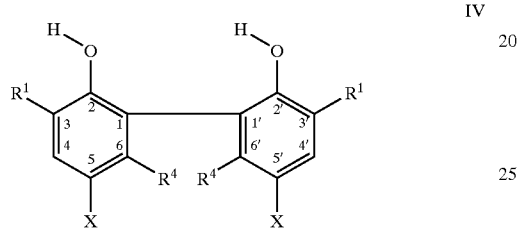

wherein $R^1$ is $C_1$ to $C_{10}$ primary or secondary alkyl or cycloalkyl, $R^4$ is $C_1$ to $C_{10}$ primary or secondary alkyl or cycloalkyl, and X is H, Cl, Br, or I comprising:
(1) when X is H
- (a) alkylating a compound of the formula V

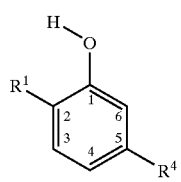

at the 4-position thereof to produce a compound of the formula VI

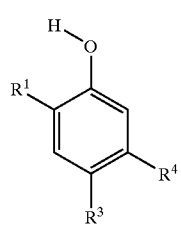

wherein $R^3$ is $C_4$ to $C_{20}$ tertiary alkyl,
- (b) oxidatively coupling the compound of the formula VI to produce a compound of the formula VII

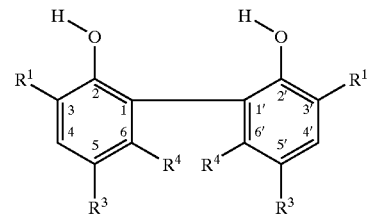

- (c) dealkylating a compound of the formula VII to produce a compound of the formula IV wherein X is H; or (2) when X is Cl, Br, or I
- (a) alkylating a compound of the formula V at the 4-position thereof to produce a compound of the formula VI,
- (b) oxidatively coupling the compound of the formula VI to produce a compound of the formula VII,
- (c) dealkylating a compound of the formula VII to produce a compound of the formula IV wherein X is H, and
- (d) substituting Cl, Br, or I, respectively, for H at the 5 and 5' positions of the compound of the formula IV wherein X is H.

In its third aspect, the present invention is a process for making a compound of the formula I

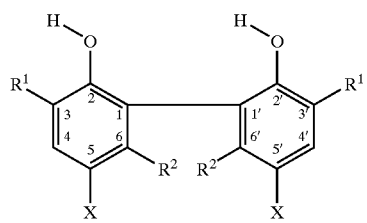

wherein $R^1$ is $C_1$ to $C_{10}$ primary or secondary alkyl or cycloalkyl, $R^2$ is $C_1$ to $C_{10}$ primary or secondary alkyl or cycloalkyl, and X is H, comprising:
- (a) oxidatively coupling a compound of the formula III

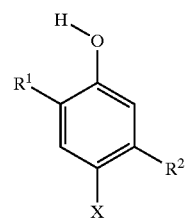

wherein X is Cl, to produce a compound of the formula I wherein X is Cl, and
- (b) dechlorinating the compound of the formula I wherein X is Cl to produce a compound of the formula I wherein X is H.

In another aspect the present invention is a compound selected from the group consisting of 3,3',6,6'-tetramethyl-2,2'-biphenol, and 3,3'-di-isopropyl-6,6'-dimentyl-2,2'-biphenol.

DETAILED DESCRIPTION OF THE INVENTION

The first aspect of the present invention provides a process for preparing 3,3',6,6'-tetraalkyl-2,2'-biphenol, comprising (1) substituting chlorine for hydrogen at the 4-position of 2,5-dialkylphenol, (2) oxidatively coupling the resulting 2,5-dialkyl-4-chloro-phenol, and (3) removing chlorine from the resulting compound. The second step is carried out by analogy with the methods of Sartori, et al (Tetrahedron, 1992, 48, 9483), but using the free phenol rather than its dichloroaluminate derivative. The three steps of the process are shown below.

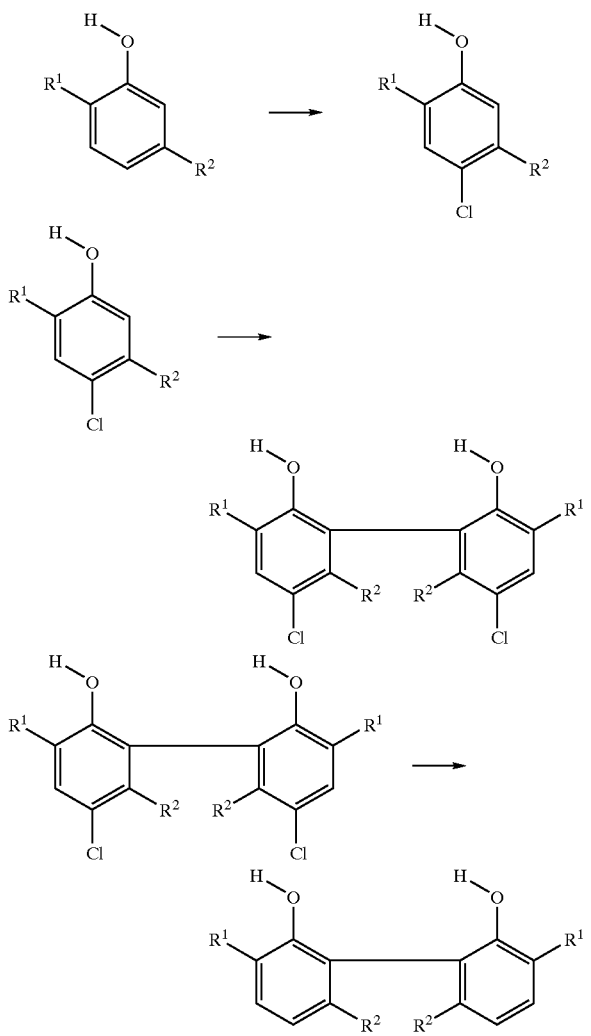

wherein $R^1$ is $C_1$ to $C_{10}$ primary or secondary alkyl or cycloalkyl; and $R^2$ is $C_1$ to $C_{10}$ primary or secondary alkyl or cycloalkyl.

Preferred $R^1$ are methyl, ethyl, n-propyl, isopropyl, n-butyl, sec-butyl, cyclohexyl, and cyclopentyl. Preferred $R^2$ are methyl and ethyl. The alkyl groups at the 2- and 5-postions may be the same or different.

In the first step of the process, a 2,5-dialkylphenol can be reacted with a chlorinating agent, such as chlorine or sulfuryl chloride, preferably in the presence of 1 to 10 mol % of a catalyst such as aluminum chloride or a diaryl sulfide such as diphenyl sulfide or a mixture thereof. See Watson, *J. Org. Chem.*, 1985, 50, 2145. The reaction may be conducted neat (without a solvent) or in a medium such as dichloromethane, chlorobenzene, or other inert solvent at a temperature between −30 and 60° C., preferably at about 25° C. The reaction is typically performed at or about atmospheric pressure for ease of operation.

In the second step of the process, the resulting 2,5-dialkyl-4-chlorophenol can be oxidatively coupled to give the corresponding dimeric chlorophenols (5,5'-dichloro-3,3',6,6'-tetraalkyl-2,2'-biphenol). The preferred method for oxidative coupling of the chlorinated phenols is by the use of an iron(III) salt, preferably ferric chloride, in a suitable polar, aprotic solvent such as dichloromethane or nitromethane, preferably nitromethane at temperature between 0° C. and 60° C., preferably about 35° C. The product is isolated by dilution with water and filtration.

In the third step of the process, dechlorination of 5,5'-dichloro-3,3',6,6'-tetraalkyl-2,2'-biphenols can be accomplished by hydrogenolytic reduction to provide the required 3,3',6,6'-tetraalkyl-2,2'-biphenols. The reduction is carried out in the presence of hydrogen gas, preferably at pressures between 1 and 50 atmospheres and temperature between 5° and 80° C., and a formate salt, such as sodium formate, and Raney® nickel or palladium catalyst such as palladium hydroxide on carbon. If a palladium catalyst is used, the reaction is generally carried out in a protic solvent such as methanol, containing 1.0 to 4.0 equivalents of an amine such as triethylamine to absorb the hydrogen chloride produced in the reaction.

The second aspect of the present invention provides a process for preparing a compound of the formula IV, comprising (1) substituting a tertiary alkyl group for hydrogen at the 4-position of 2,5-dialkylphenol, (2) oxidatively coupling the resulting 2,5-dialkyl-4-tert-alkyl-phenol, and (3) removing the tertiary alkyl group from the resulting compound. The three steps of the process are shown below.

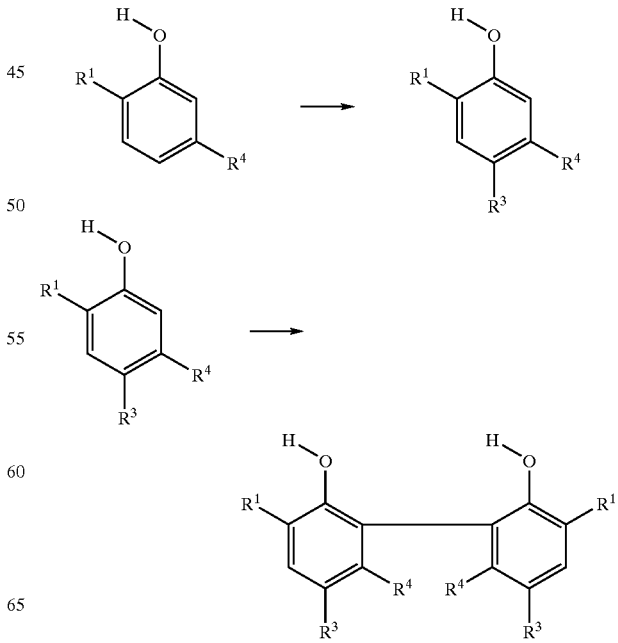

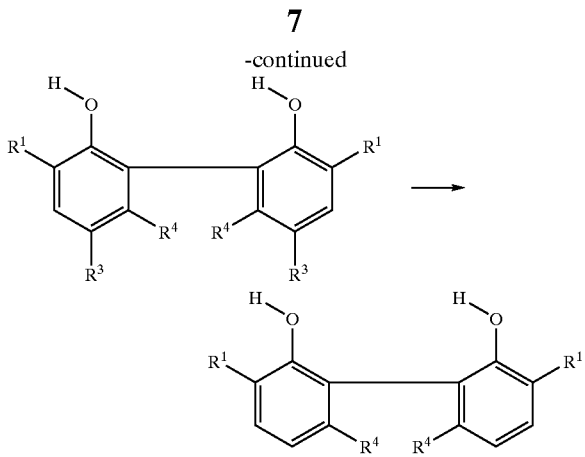

wherein $R^1$ is $C_1$ to $C_{10}$ primary or secondary alkyl or cycloalkyl; $R^4$ is $C_1$ to $C_{10}$ primary or secondary alkyl or cycloalkyl; and $R^3$ is $C_4$ to $C_{20}$ tertiaryl alkyl.

In the first step of the process, a 2,5-dialkylphenol can be reacted with a tert-alkyl halide in the presence of a Lewis Acid catalyst, such as zinc chloride or aluminum chloride, to give a 2,5-dialkyl-4-tert-alkylphenol. Alternatively, the 2,5-dialkyl-4-tert-alkylphenol can be prepared from contacting 2,5-dialkylphenol with 2,2-dialkylethylene in the presence of an acid catalyst. An example of the alternative method is the incorporation of a tert-butyl group into the 4-position of 2,5-dialkylphenol by reacting 2,5-dialkylphenol with isobutylene in the presence of sulfuric acid.

In the second step of the process, 2,5-dialkyl-4-tert-alkylphenol can be oxidatively coupled using a copper diamine catalyst and oxygen as the oxidizing agent.

The copper diamine catalyst can be prepared using the procedure described in the Tetrahedron Letters, 1994, 35, 7983. A copper halide, such as CuCl, CuBr, CuI, or CuCl$_2$, is added to a mixture of alcohol, such as methanol, and water and the diamine is slowly added. After the addition of the diamine, air is sparged through the mixture with vigorous stirring. The catalyst is filtered. Additional catalyst can be obtained by concentrating the filtrate and filtering the desired catalyst. The catalyst can also be prepared in situ by contacting the copper halide and the diamine in the solvent for the coupling reaction. Suitable solvents for the oxidative coupling of tri and tetrasubstituted phenols are methylene chloride and aromatic solvents such as xylene, benzene and toluene. Example of diamines include, but are not limited to, the following: N,N,N',N'-tetraethylethylene diamine, N,N,N',N'-tetraethyl-1,3-propanediamine, N,N,N',N'-tetraethylmethane diamine, N,N,N',N'-tetramethyl-1,6-hexanediamine, N,N,N',N'-tetramethyl-1,3-propanediamine, dipiperidinomethane, N,N,N',N'-tetramethylethylene diamine and 1,4-diazabicyclo-(2,2,2)-octane. Preferrably, the diamine is N,N,N',N'-tetramethylethylene diamine.

In the third step of the process, the 3,3',6,6'-tetraalkyl-5,5'-di-tert-alkyl-2,2'-biphenol can be dealkylated by contacting it with a strongly acidic catalyst, such as an alkyl- or arylsulfonic acid, sulfuric acid, phosphoric acid, aluminum chloride, or the like, optionally in the presence of a solvent such as toluene, chlorobenzene, nitromethane, or xylene, typically at temperatures between 10 and 150° C.

The oxidative coupling can be carried out neat (without a solvent) or using one or more of a wide range of poorly oxidizable solvents including dichloromethane, chlorobenzene, toluene, xylenes, nitromethane, paraffins, etc. Static air, air-flow, or oxygen can be used as oxidants in the oxidative coupling.

The third aspect of the present invention provides a process for making a compound of the formula I

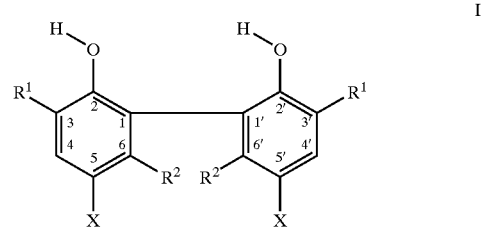

wherein $R^1$ is $C_1$ to $C_{10}$ primary or secondary alkyl or cycloalkyl, $R^2$ is $C_1$ to $C_{10}$ primary or secondary alkyl or cycloalkyl, and X is H, comprising:
(a) oxidatively coupling a compound of the formula III

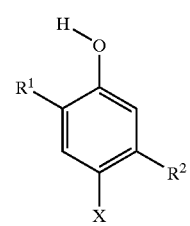

wherein X is Cl, to produce a compound of the formula I wherein X is Cl, and (b) dechlorinating the compound of the formula I wherein X is C to produce a compound of the formula I wherein X is H.

In the first step of the process, the resulting 2,5-dialkyl-4-chlorophenol can be oxidatively coupled to give the corresponding dimeric chlorophenols (5,5'-dichloro-3,3',6,6'-tetraalkyl-2,2'-biphenol). The preferred method for oxidative coupling of the chlorinated phenols is by the use of an iron(III) salt, preferably ferric chloride, in a suitable polar, aprotic solvent such as dichloromethane or nitromethane, preferably nitromethane at temperature between 0° C. and 60° C., preferably about 35° C. The product is isolated by dilution with water and filtration.

In the second step of the process, dechlorination of 5,5'-dichloro-3,3',6,6'-tetraalkyl-2,2'-biphenols can be accomplished by hydrogenolytic reduction to provide the required 3,3',6,6'-tetraalkyl-2,2'-biphenols. The reduction is carried out in the presence of hydrogen gas, preferably at pressures between 1 and 50 atmospheres and temperature between 5° and 80° C., and a formate salt, such as sodium formate, and Raney® nickel or palladium catalyst such as palladium hydroxide on carbon. If a palladium catalyst is used, the reaction is generally carried out in a protic solvent such as methanol, containing 1.0 to 4.0 equivalents of an amine such as triethylamine to absorb the hydrogen chloride produced in the reaction.

In the first, second and third aspects of the present invention, a 3,3',6,6'-tetraalkyl-5,5'-dihalo-2,2'-biphenol may be halogenated at the para positions of 3,3',6,6'-tetraalkyl-2,2'-biphenol, as shown below,

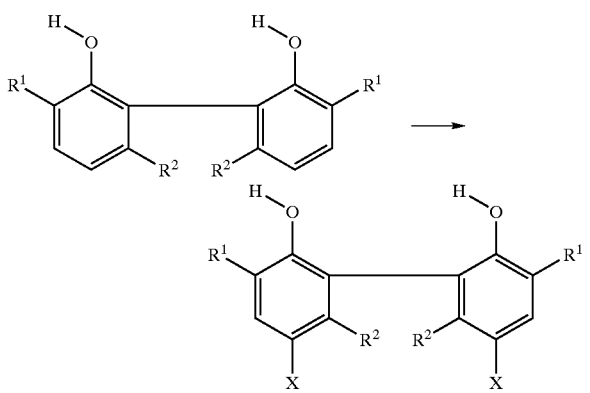

wherein $R^1$ is $C_1$ to $C_{10}$ primary or secondary alkyl or cycloalkyl; $R^2$ is $C_1$ to $C_{10}$ primary or secondary alkyl or cycloalkyl; and X is Cl, Br or I.

Addition of Br to 3,3',6,6'-tetraalkyl-2,2'-biphenols can be accomplished by reaction of $Br_2$ in a suitable solvent. Typical solvents for bromination are low polarity solvents such as chloroform, dichloromethane, carbon tetrachloride, and carbon disulfide. In some cases, aqueous bromine can be used. The preferred process is one carried out in a low polarity solvent. This reaction can be accomplished at −10° C. to 50° C., preferably at room tempearature.

The compounds which are produced by the processes of the present invention can be used as reactants to make phosphorous-containing ligands that are useful to make catalysts that, in turn, are useful in both hydrocyanation and hydroformylation reactions. Bidentate phosphite ligands are particularly useful.

Bidentate phosphite ligands can be prepared as described in U.S. Pat. No. 5,235,113 by contacting phosphorochloridites with the biphenol compounds made by the processes of the present invention. More recent U.S. Pat. Nos. 6,031,120 and 6,069,267, incorporated herein by reference, describe selective synthesis of bidentate phosphite ligands in which a phosphorochloridite is prepared in-situ from phosphorus trichloride and a phenol such as o-cresol and then treated in the same reaction vessel with an aromatic diol to give the bidentate phosphite ligand. The biphenols of the present invention are substituted for the aromatic diol.

The compounds which are produced by the processes of the present invention can be polymerized and then used as reactants to make phosphorous-containing ligands that are useful to make catalysts that, in turn, are useful in both hydrocyanation and hydroformylation reactions.

The compounds made by the processes of the present invention, in which X is H, can be used to make polymeric ligands by a process which comprises: (1) reacting the compounds made by the processes of the present invention, in which X is H, with a compound containing at least two benzyl chloride groups, in the presence of a Lewis acid catalyst, and (2) reacting the product of step (1) with at least one phosphorochloridite compound in the presence of an organic base. Preferably the Lewis acid catalyst is zinc chloride or aluminum chloride, and the organic base is a trialkylamine.

The compounds made by the processes of the present invention, in which X is Cl, Br, or I, can be used to make polymeric ligands by a process which comprises:

(1) protecting the OH groups by substituting a lower alkyl protecting group for H on the OH groups to make a protected compound, (2) treating the protected compound with a compound containing at least two boronic groups in the presence of a Group VIII transition metal catalyst, (3) replacing the protecting group of the product from step (2) with hydrogen, and (4) reacting the product of step (3) with at least one phosphorochlorodite compound in the presence of an organic base.

Preferably, the Group VIII transition metal is palladium, nickel or copper and the organic base is a trialkylamine compound in which the alkyl group is a $C_1$ to $C_{12}$ branched or straight chain alkyl group. More preferably the organic base is triethylamine.

Two particularly important industrial catalytic reactions using phosphorus-containing ligands are olefin hydrocyanation and isomerization of branched nitrites to linear nitrites. See, for example, U.S. Pat. Nos. 5,512,695 and 5,512,696, and International Patent Application WO9514659. Phosphite ligands are particularly useful for both reactions. The hydrocyanation of unactivated and activated ethylenically unsaturated compounds (olefins) using transition metal complexes with monodentate and bidentate phosphite ligands is well known. Bidentate phosphinite and phosphonite ligands are useful as part of a catalyst system for the hydrocyanation of ethylenically unsaturated compounds. Bidentate phosphinite ligands are also useful as part of a catalyst system for the hydrocyanation of aromatic vinyl compounds.

Hydroformylation is another industrially useful process that utilizes catalysts made from phosphorus- containing ligands. The use of phosphine ligands, including diphosphines, is known for this purpose. The use of catalysts made from phosphite ligands is also known. Such catalysts usually contain a Group VIII metal. See for example, U.S. Pat. No. 5,235,113.

Two particularly useful compounds that can be made by the present processes are 3,3',6,6'-tetramethyl-2,2'-biphenol and 3,3'-di-isopropyl-6,6'-dimentyl-2,2'-biphenol.

EXAMPLES

The following non-limiting examples illustrate the present invention. All parts, proportions, and percentages are by weight, unless otherwise indicated.

Example 1

Process in Accordance With the First Aspect of the Invention for Preparing 3,3',6,6'-Tetramethyl-2,2'-biphenol First Step of the Process: Preparation of 4-Chloro-2,5-Xylenol:

To a solution of 100 g (0.82 mol) of 2,5-xylenol and 0.9 g of diphenyl sulfide in 700 mL of dichloromethane was added a solution of 106 g (0.79 mol) of sulfuryl chloride in 100 mL of dichloromethane, maintaining the temperature at 5–15° C. The mixture was stirred for an additional hour and then poured onto 400 g of ice-water containing 5 g of sodium bisulfite. The layers were separated, and the organic phase was washed with water, dried ($MgSO_4$), and concentrated to dryness. The crude solids were slurried with a minimum amount of hexanes, filtered, and suction-dried to give 121 g (94%) of product, homogeneous by Thin Layer Chromatography (TLC), GC, and $^1$H-NMR analysis. $^1$H-NMR ($CDCl_3$) δ 2.18 (s, 3H), 2.27 (s, 3H), 4.61 (s, 1H), 6.63 (s, 1H), 7.07 (s, 1H). Lit (Blackstock, *Aust. J. Chem.* 1973, 26, 775): mp 74–75° C.

Second Step of the Process: Preparation of 5,5'-Dichloro-3, 3',6, 6'-Tetramethyl-2,2'-Biphenol To a mechanically-stirred mixture of 71.4 g (0.458 mol) of 4-chloro-2,5-xylenol and 120 mL of nitromethane was added 94 g (0.59 mol) of anhydrous ferric chloride in 5 portions over about 20 minutes with cooling to maintain the temperature below 35° C. The mixture was stirred for an additional 3 hours and then 300 mL of ice water containing 50 mL of concentrated HCl was added, followed by 300 mL of hexanes. The mixture was filtered, and the solids were washed with water and hexanes and dried in vacuo to give 51.0 g of product. The organic phase was separated from the filtrate, washed with water, and concentrated; the residue was then slurried in hexanes and filtered to give another 11 g of product. The total yield was thus 62 g (87%) of a tan solid (mp 148–155° C.). Additional purification to remove traces of iron helps facilitate the subsequent reductive dechlorination. Purification could be accomplished by dissolving in ethyl acetate, washing this solution with aqueous ethylenediamine-tetraacetic acid disodium salt (EDTA-2Na, EDTA=ethylenediaminetetraacetic acid), drying (MgSO$_4$), concentration and washing with hexanes to afford off-white material with mp 164° C. $^1$H-NMR (CDCl$_3$) δ 1.98 (s, 3H), 2.25 (s, 3H), 4.60 (s, 1H), 7.25 (s, 1H).

Third Step of the Process: Preparation of 3,3',6,6'-Tetramethyl-2,2'-Biphenol:

A sample of purified 5,5'-dichloro-3,3',6,6'-tetramethyl-2, 2'-biphenol (15.0 g, 48.4 mmol) was dissolved in 100 mL of ethanol containing 10 mL of water and 20 mL of triethylamine. This solution was added to 1.0 g (dry weight basis) of moist 20% Pd(OH)$_2$/C (Pearlman's catalyst) and hydrogenated at 50 psig for 2 hours at ambient temperature. The product was isolated by filtration of catalyst, concentration, dissolution of the residue in EtOAc, washing with water, and concentration to dryness to give 11.0 g (94%) of product, mp 110–113° C. $^1$H-NMR (CDCl$_3$) δ 1.95 (s, 3H), 2.25 (s, 3H), 4.71 (s, 1H), 6.81 (d, 1H, J=7.5 Hz), 7.10 (d, 1H, J=7.5 Hz).

The second and third steps of the foregoing example also illustrate the third aspect of the invention.

Example 2

Process in Accordance With the Third Aspect of the Invention for Preparing 3,3'-di-Isopropyl-6,6'-dimethyl-2,2'-biphenol First Step of the Process: Preparation of 5,5'-Dichloro-3,3'-diisopropyl-6,6'-dimethyl-2,2'-biphenol:

A well-stirred mixture of 36.0 g (0.195 mol) of chlorothymol and 50 mL of nitromethane was cooled to 5° C. and 40 g (0.25 mol) of anhydrous ferric chloride was added over 20 minutes. The mixture was allowed to warm to ambient temperature and held an additional hour. Ice-water (300 mL) was added all at once, and the mixture was concentrated at reduced pressure to remove about 100 mL of the nitromethane-water azeotrope. The solids were filtered and recrystallized from aqueous isopropanol to give 23.3 g of a first crop and 3.9 g of a second crop of solids, mp 98° C. $^1$H-NMR (CDCl$_3$) δ 1.24 (two d, 6H, J=7 Hz), 1.98 (s, 3H), 3.26 (septet, 1H, J=7 Hz), 4.63 (s, 1H), 7.30 (s, 1H).

Second Step of the Process: 3,3'-di-Isopropyl,6,6'-dimethyl-2,2'-biphenol:

This substituted biphenol was prepared similarly to the third step of Example 1 except 5,5'-dichloro-3,3'-diisopropyl-6,6'-dimethyl-2,2'-biphenol was used instead of 5,5'-dichloro-3,3',6, 6'-tetramethyl-2,2'-biphenol, mp 89–92° C. $^1$H-NMR (CDCl$_3$) δ 1.25 (d, 6H), 1.95 (s, 3H), 3.28 (septet, 1H), 4.76 (s, 1H), 6.88 (d, 1H, J=7.5 Hz), 7.18 (d, 1H, J=7.5 Hz).

Example 3

Process in Accordance With the Second Aspect of the Invention for Preparing 3,3',6,6'-Tetramethyl-2, 2'-biphenol First Step of the Process: Preparation of 4-t-Butyl-2,5-xylenol Preparation of 4-t-Butyl-2,5-xylenol: 2,5-Xylenol (90 g, 0.73 mol) was melted at 80° C., 1 mL of concentrated sulfuric acid was added, and the mixture was heated at 90° C. while isobutylene gas was introduced subsurface over 4 hours. The reaction appeared to stall at about 80% conversion. The reaction mass was diluted with water and neutralized with NaHCO$_3$, and some starting xylenol was removed by steam-distillation. Since the steam-distillation did not completely remove the starting material, the residue was dissolved in hot hexanes, separated from the aqueous phase, and cooled in an ice-bath. The precipitated product was filtered and washed with cold hexanes to give 64 g (49%) of 4-t-Butyl-2,5-xylenol; lit. (Stevens, *Ind. Eng. Chem.* 1943, 655; Parc, *Rev. Inst. Fr. Pet.* 1960, 680) mp 70–72° C. $^1$H-NMR (CDCl$_3$) δ 1.37, (s, 9H), 2.20 (s, 3H), 2.43 (s, 3H), 4.85 (s, 1H), 6.53 (s, 1H), 7.08 (s, 1H).

Second Step of the Process: Preparation of 5,5'-Bis(t-butyl)-3,3',6,6'-tetramethyl-2,2'-biphenol:

To a solution of 18.6 g (0.104 mol) of 4-t-butyl-2,5-xylenol in 20 mL of dichloromethane was added 0.6 g (3 mmol) of copper chlorohydroxide-TMEDA complex (TMEDA=tetramethylethylenediamine). The dark purple mixture was stirred under ambient air overnight. Gas chromatography (GC) analysis showed only 25% conversion, so the mixture was diluted with dichloromethane, dried (MgSO$_4$) and concentrated to dryness. To the crude residue was added 20 mL of cyclohexane and 1.2 g (6 mmol) of the above copper chlorohydroxide-TMEDA catalyst, and the mixture was stirred under air at ambient temperature for three days (85% conversion). The purple solution was concentrated to dryness, and the residue was chromatographed on silica gel to give 10.2 g (55%) of pure 5,5'-Bis (t-butyl)-3,3',6,6'-tetramethyl-2,2'-biphenol, mp 103–105° C. $^1$H-NMR (CDCl$_3$) δ 1.42, (s, 9H), 2.06 (s, 3H), 2.25 (s, 3H), 4.54 (s, 1H), 6.51 (s, 1H), 7.24 (s, 1H).

Third Step of the Process: Preparation of 3,3',6,6'-Tetramethyl-2,2'-biphenol:

To a 50 mL flask were added 0.5 g of 5,5'-Bis(t-butyl)-3,3',6,6'-tetramethyl-2,2'-biphenol, 5 mL of xylenes and 0.05 g of p-toluenesulfonic acid. The mixture was refluxed for about 2 hours. The mixture was cooled and water added. The mixture was extracted with hexanes; the organic layer was washed with water and dried over MgSO$_4$. After removing the solvent, the residue was recrystallized from petroleum ether.

Example 4

Process in Accordance With the Second Aspect of the Invention for Preparing 5,5'-Di-t-butyl-3,3'-di-isoprbpyl,6,6'-dimethyl-2,2'-biphenol First Step of the Process: Preparation of 4-t-Butylthymol:

To 30 g (0.20 mol) of thymol, heated at 60° C. under nitrogen, was added 1 g of concentrated sulfuric acid. After heating to 90° C., a slow stream of isobutylene was introduced over about 2 hours. The reaction stalled at about 50% conversion, so an additional charge of sulfuric acid was added and the reaction was monitored by GC-analysis until approximately 70–80% conversion was achieved. The reaction was worked up as in Example 1 and the crude residue was recrystallized from hexanes to give 20 g of 4-t- butylthymol, mp 68–69° C., lit (U.S. Pat. No. 4,880,775): mp 76–77° C. $^1$H-NMR (CDCl$_3$) δ 1.25 (d, 6H, J=7 Hz), 1.38, (s, 9H), 2.44 (s, 3H), 3.15 (septet, 1H), 4.49 (s, 1H), 6.51 (s, 1H), 7.18 (s, 1H).

Second Step of the Process: Preparation of 5,5'-Di-t-butyl-3,3'-di-isopropyl,6,6'-dimethyl-2,2'-biphenol:

To a solution of 20 g (0.104 mol) of 4-t-butylthymol in 50 mL of dichloromethane was added 1.0 g (5 mmol) of copper chlorohydroxide-TMEDA complex and the dark purple mixture was allowed to stir under ambient air for three days (50% conversion). The mixture was diluted with hexanes, washed with aqueous EDTA solution, dried (MgSO$_4$) and concentrated to dryness. The residue was chromatographed on silica gel to give 3.6 g (34% based on conversion) of pure dimer 5,5'-Di-t-butyl-3,3'-di-isopropyl,6,6'-dimethyl-2,2'-biphenol, mp 105–108° C. $^1$H-NMR (CDCl$_3$) δ 1.26 (d, 6H) 1.43, (s, 9H), 3.25 (septet, 1H), 4.58 (s, 1H), 7.30 (s, 1H).

Debutylating 5,5'-di-t-Butyl-3,3'-diisopropyl-6,6'-dimethyl-2,2'-biphenol

A 500-mL resin kettle equipped with mechanical stirrer and condenser was placed in an oil bath and charged with 153 g of a mixture of 5,5'-di-t-butyl-3,3'-diisopropyl-6,6'-dimethyl-2,2'-biphenol in a hydrocarbon solvent. By gas chromatography analysis, the mixture was 15.0% 5,5'-di-t-butyl-3,3'-di-isopropyl,6,6'-dimethyl-2,2'-biphenol. 1.5 g p-toluenesulfonic acid was charged, and the mixture was heated to 130° C. After 7.5 hours, gas chromatography analysis showed the mixture contained 11.6% fully debutylated product, 3,3'-diisopropyl-6,6'-dimethyl-2,2'-biphenol; 2.7% mono-debutylated product, 5-t-butyl-3,3'-diisopropyl-6,6'-dimethyl-2,2'-biphenol; and 0.3% unreacted starting material.

Example 5

Bromination of 2,2'-Dihydroxy-3,3'-diisopropyl-5,5'-dimethylbiphenyl

Under an atmosphere of nitrogen, Br$_2$ (3.36 mL, 0.0652 mol) in CH$_2$Cl$_2$ (5 mL) was added dropwise to a CH$_2$Cl$_2$ (200 mL) solution of 2,2'-dihydroxy-3,3'-diisopropyl-5,5'-dimethylbiphenyl (6.488 g, 0.0217 mol). The resulting mixture was stirred at room temperature overnight. After the reaction was complete, the mixture was washed with 10% NaHSO$_3$ (3×50mL) followed by brine (2×50 mL) and dried over MgSO$_4$. The solvent was removed under vacuum to afford an orange oil, which was purified by column chromatography.(silica gel, 10% EtOAc/hexane). Yield of light-brown solid was 3.95 g (40%). $^1$H NMR (C$_6$D$_6$): 1.07 (d, 6H), 1.89 (s, 3H), 3.17 (m, 1H) 4.30 (br s, 1H), 7.52 (s, 1H).

What is claimed is:

1. A process for making a compound of the formula IV

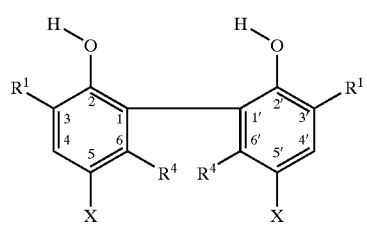

IV wherein
R$^1$ is C$_1$ to C$_{10}$ primary or secondary alkyl or cycloalkyl,
R$^4$ is C$_1$ to C$_{10}$ primary or secondary alkyl or cycloalkyl, and
X is H, Cl, Br, or I
comprising:
(1) when X is H
(a) alkylating a compound of the formula V

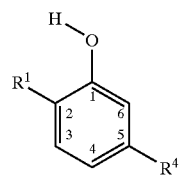

V at the 4-position thereof to produce a compound of the formula VI

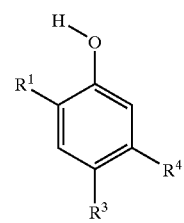

VI wherein R$^3$ is C$_4$ to C$_{20}$ tertiary alkyl,
(b) oxidatively coupling the compound of the formula VI to produce a compound of the formula VII

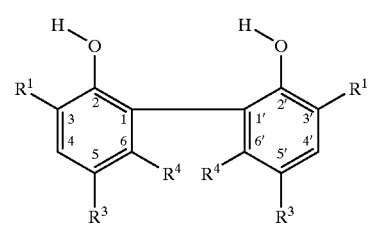

VII (c) dealkylating a compound of the formula VII to produce a compound of the formula IV wherein X is H; and
(2) when X is Cl, Br, or I
(a) alkylating a compound of the formula V at the 4-position thereof to produce a compound of the formula VI,
(b) oxidatively coupling the compound of the formula VI to produce a compound of the formula VII,
(c) dealkylating a compound of the formula VII to produce a compound of the formula IV wherein X is H, and
(d) substituting Cl, Br, or I, respectively, for H at the 5 and 5' positions of the compound of the formula IV wherein X is H.

2. The process of claim 1 wherein the alkylating step is carried out by reacting the compound of the formula V with a tert-alkyl halide in the presence of a Lewis Acid catalyst.

3. The process of claim 2 wherein the Lewis Acid catalyst is zinc chloride or aluminum chloride.

4. The process of claim 1 wherein the alkyating step is carried out by reacting the compound of the formula V with a 2,2-dialkylethylene in the presence of an acid catalyst.

5. The process of claim 1 wherein the oxidative coupling step is carried out by exposing the compound of the formula VI to oxygen and a copper diamine catalyst.

6. The process of claim 1 wherein the dealkylating step is carried out by contacting the compound of the formula VII with a strong acid selected from the group consisting of alkylsulforic acid, arylsulforic acid, sulfuric acid, phosphoric acid, and aluminum chloride.

7. The process of claim 6 wherein the strong acid is selected from the group consisting of alkylsulfonic acid, arylsulfonic acid, sulfuric acid, phosphoric acid, and aluminum chloride.

* * * * *